(12) United States Patent
Walther et al.

(10) Patent No.: US 8,273,046 B2
(45) Date of Patent: Sep. 25, 2012

(54) SYSTEMS AND METHODS FOR PROVIDING LIGHT THERAPY TRACTION

(75) Inventors: Jay Walther, West Jordan, UT (US); Scott Davis, Bountiful, UT (US); Ian Brown, Orem, UT (US); Scott Mabey, West Bountiful, UT (US); Chris Spencer, Riverton, UT (US); Larry Beardall, Sandy, UT (US); Gary Whatcott, Holladay, UT (US)

(73) Assignee: Dynatronics Corporation, Salt Lake City, UT (US)

( * ) Notice: Subject to any disclaimer, the term of this patent is extended or adjusted under 35 U.S.C. 154(b) by 288 days.

(21) Appl. No.: 12/422,114

(22) Filed: Apr. 10, 2009

(65) Prior Publication Data

US 2010/0094190 A1    Apr. 15, 2010

Related U.S. Application Data

(62) Division of application No. 11/368,017, filed on Mar. 3, 2006, now abandoned.

(51) Int. Cl.
  *A61F 13/06* (2006.01)
  *A61F 5/00* (2006.01)
  *A61H 7/00* (2006.01)
  *A61H 1/00* (2006.01)
  *A61H 1/02* (2006.01)
  *A61H 5/00* (2006.01)
  *A61B 18/18* (2006.01)
  *A61N 5/06* (2006.01)

(52) U.S. Cl. .................. 602/32; 128/898; 601/7; 601/9; 601/15; 602/2; 606/2; 606/10; 606/13; 607/88; 607/89; 607/91; 607/94; 607/95

(58) Field of Classification Search .......... 602/2, 32–40; 607/88–95; 601/7, 9, 15; 606/9, 13, 16, 606/17, 23, 2, 10; 128/898
See application file for complete search history.

(56) References Cited

U.S. PATENT DOCUMENTS

| | | |
|---|---|---|
| 3,096,768 A | 7/1963 | Griffith, Jr. |
| 3,774,620 A | 11/1973 | Hansjurgens |
| 3,895,639 A | 7/1975 | Rodler |
| 3,958,577 A | 5/1976 | Rodler |
| 4,023,574 A | 5/1977 | Nemec |
| 4,071,033 A | 1/1978 | Nawracaj et al. |
| 4,153,061 A | 5/1979 | Nemec |
| 4,280,504 A | 7/1981 | Rodler |
| 4,368,410 A | 1/1983 | Hance et al. |
| 4,535,777 A | 8/1985 | Castel |
| 4,538,598 A | 9/1985 | Gill et al. |
| 4,564,019 A | 1/1986 | Miwa |

(Continued)

*Primary Examiner* — Patricia Bianco
*Assistant Examiner* — Brandon L Jackson
(74) *Attorney, Agent, or Firm* — Kirton McConkie; David B. Tingey

(57) ABSTRACT

Systems and methods for providing light therapy traction to a patient. A light therapy device and a traction mechanism provide concurrent, alternating and/or repetitive treatment to a patient. The light therapy device includes one or more light sources configured to deliver light to a patient. The traction mechanism is configured to provide selective separation to a particular location the patient's body, such as a location of the patient's vertebrae. In some embodiments, the light therapy and traction are performed simultaneously. In other embodiments, the light therapy and lumbar traction are performed in treatment cycles to the patient. Embodiments of the present invention embrace the application of light therapy prior to, during, and/or after a cervical and/or lumbar traction treatment.

20 Claims, 5 Drawing Sheets

U.S. PATENT DOCUMENTS

| | | |
|---|---|---|
| 4,690,144 A | 9/1987 | Rise et al. |
| 4,747,820 A | 5/1988 | Hornlein et al. |
| 4,768,496 A | 9/1988 | Kreizman et al. |
| 4,848,347 A | 7/1989 | Hall |
| 4,930,504 A | 6/1990 | Diamantopoulos et al. |
| 4,966,131 A | 10/1990 | Houghton et al. |
| RE33,672 E | 8/1991 | Miwa |
| 5,151,085 A | 9/1992 | Sakurai et al. |
| 5,184,605 A | 2/1993 | Grzeszykowski |
| 5,269,304 A | 12/1993 | Matthews |
| 5,460,595 A | 10/1995 | Hall et al. |
| 5,464,436 A | 11/1995 | Smith |
| 5,512,057 A | 4/1996 | Reiss et al. |
| 5,620,481 A | 4/1997 | Desai et al. |
| 5,776,173 A | 7/1998 | Madsen, Jr. et al. |
| 5,995,873 A | 11/1999 | Rhodes |
| 6,108,197 A | 8/2000 | Janik |
| 6,197,020 B1 | 3/2001 | O'Donnell, Jr. |
| 6,252,714 B1 | 6/2001 | Guenther et al. |
| 6,393,328 B1 | 5/2002 | McGraw et al. |
| 6,560,487 B1 | 5/2003 | McGraw et al. |
| 6,728,036 B2 | 4/2004 | Kleemann et al. |
| 6,826,429 B2 | 11/2004 | Johnson et al. |
| 6,841,738 B2 | 1/2005 | Michiwaki et al. |
| 6,909,546 B2 | 6/2005 | Hirai |
| 6,942,658 B1 | 9/2005 | Rizoiu et al. |
| 7,077,544 B2 | 7/2006 | Parker |
| 7,118,563 B2 | 10/2006 | Weckwerth et al. |
| 7,189,214 B1 | 3/2007 | Saunders |
| 7,374,569 B2 | 5/2008 | Whatcott et al. |
| 2004/0010299 A1* | 1/2004 | Tolkoff et al. .................. 607/88 |
| 2004/0136665 A1 | 7/2004 | Furman et al. |
| 2004/0184287 A1 | 9/2004 | Smith et al. |
| 2004/0260367 A1 | 12/2004 | De Taboada et al. |
| 2005/0234527 A1 | 10/2005 | Slatkine |
| 2006/0100676 A1 | 5/2006 | Walmsley |
| 2006/0173514 A1 | 8/2006 | Biel et al. |
| 2006/0287627 A1 | 12/2006 | Johnson |
| 2007/0106192 A1* | 5/2007 | Johnson .......................... 602/32 |
| 2007/0208289 A1 | 9/2007 | Walther et al. |
| 2007/0208396 A1 | 9/2007 | Whatcott et al. |

* cited by examiner

SYSTEMS AND METHODS FOR PROVIDING LIGHT THERAPY TRACTION

RELATED APPLICATIONS

This application claims priority to and is a divisional of U.S. patent application Ser. No. 11/368,017 filed Mar. 3, 2006 entitled SYSTEMS AND METHODS FOR PROVIDING LIGHT THERAPY TRACTION (abandoned), which is incorporated herein by reference.

BACKGROUND OF THE INVENTION

1. Field of the Invention

The present invention relates to optimizing traction treatment. In particular, the present invention relates to systems and methods for providing light therapy cervical and/or lumbar traction to a patient.

2. Background and Related Art

When a patient has a bulging disc in his/her vertebrae and puts pressure on the nearby nerve, the patient typically experiences pain down his/her leg. Attempts have been made to provide a treatment that could be performed by a caregiver on the patient to help alleviate such discomfort.

One treatment that is available to caregivers, such as therapists and chiropractors, to treat such bulging discs is to provide traction. This treatment technique includes placing the patient in a harness system and stretching the patient to relieve the pressure and to obtain separation between the disc spaces.

However, while this technique of traction currently exists to treat bulging discs, challenges still exist. For example, if the patient is not relaxed during traction, the technique is not as effective and can potentially strain the patient. Accordingly, it would be an improvement in the art to augment or even replace the current techniques with other techniques to more effectively treat a patient.

SUMMARY OF THE INVENTION

The present invention relates to optimizing traction treatment. In particular, the present invention relates to systems and methods for providing light therapy cervical and/or lumbar traction to a patient.

Implementation of the present invention takes place in association with a light therapy device and a traction mechanism, such as a cervical and/or lumbar traction treatment system. The light therapy device is, for example, a hand-held device, a pad, a scanner, or other attended or unattended light source that includes one or more light sources configured to deliver light to a patient. For example, the lumbar traction mechanism is configured to provide selective separation to a particular location of a patient's vertebrae. Different angles are utilized for different positions of the patient's spine and/or for posterior or anterior conditions. The angle of traction focuses the treatment to a specific area of the spine. The angle of pull can be particular to the type of condition.

Light therapy is performed in combination with traction to provide increased benefits. The light therapy provides, for example, a relaxation of muscles, a relaxation of muscle spasms, and/or temporary relief of pain, stiffness, and muscle joint aches. Eliminating or otherwise reducing tension, stress, stiffness, and/or pain provides for enhanced traction results. In some implementations, the light therapy and traction are performed simultaneously. In other implementations, the light therapy is performed before and/or after traction treatment. In some implementations, the light therapy and traction treatment is performed in treatment cycles.

While the methods and processes of the present invention have proven to be particularly useful in the area of treating a bulging disc of a patient's vertebrae or back pain, those skilled in the art can appreciate that the methods and processes can be used in a variety of different applications. For example, such applications or treatments relate to degenerative disc disease, posterior facet syndrome, sciatica, structural pressures, soft tissue hypomobility, lateral stenosis, foraminal closure, and other conditions relating to the spine.

Additional examples of treatment in accordance with the present invention include use of the systems and/or methods of the present invention for the treatment of an injury, tension headaches, chronic pain, migraine headaches, tension headaches, atypical facial pain, TMJ disorders, occipital neuralgia, neck-shoulder pain, fibromyalgia, medial epicondylitis, lateral epicondylitis, carpal tunnel syndrome, osteoarthritis, rheumatoid arthritis, pain and/or stiffness associated with arthritis, muscle spasm, costochondritis, spondylitis, low back strain, joint pain, sciatica, Achilles tendonitis, ankle sprain, plantar fasciitis, shingles, Raynaud's Syndrome, reflex sympathetic dystrophy (also known as chronic regional pain syndrome), postherpetic neuralgia, burns, inflammation, pain, muscle spasm, wound healing, and the like.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

The present invention relates to optimizing traction treatment. In particular, the present invention relates to systems and methods for providing light therapy cervical and/or lumbar traction to a patient.

Embodiments of the present invention take place in association with a light therapy device and a traction mechanism, such as a lumbar and/or cervical traction mechanism. The light therapy device is, for example, a hand-held device, a pad, a scanner, or other therapeutic lamp that includes one or more light sources configured to deliver light to a patient. The lumbar traction mechanism, for example, is configured to provide selective separation to a particular location of a patient's vertebrae.

A combination of light therapy and traction provides enhanced treatment results. For example, a patient may experience an increased relaxation of muscles, an increased relaxation of muscle spasms, and/or an increased relief of pain, stiffness, and aches. Such relaxation, relief from pain stiffness and aches provides a more effective traction treatment.

In some embodiments of the present invention, the light therapy and traction are performed simultaneously. In other embodiments, the light therapy is performed before and/or after traction treatment. In some embodiments, the light therapy and traction are performed in treatment cycles.

Figure 1:
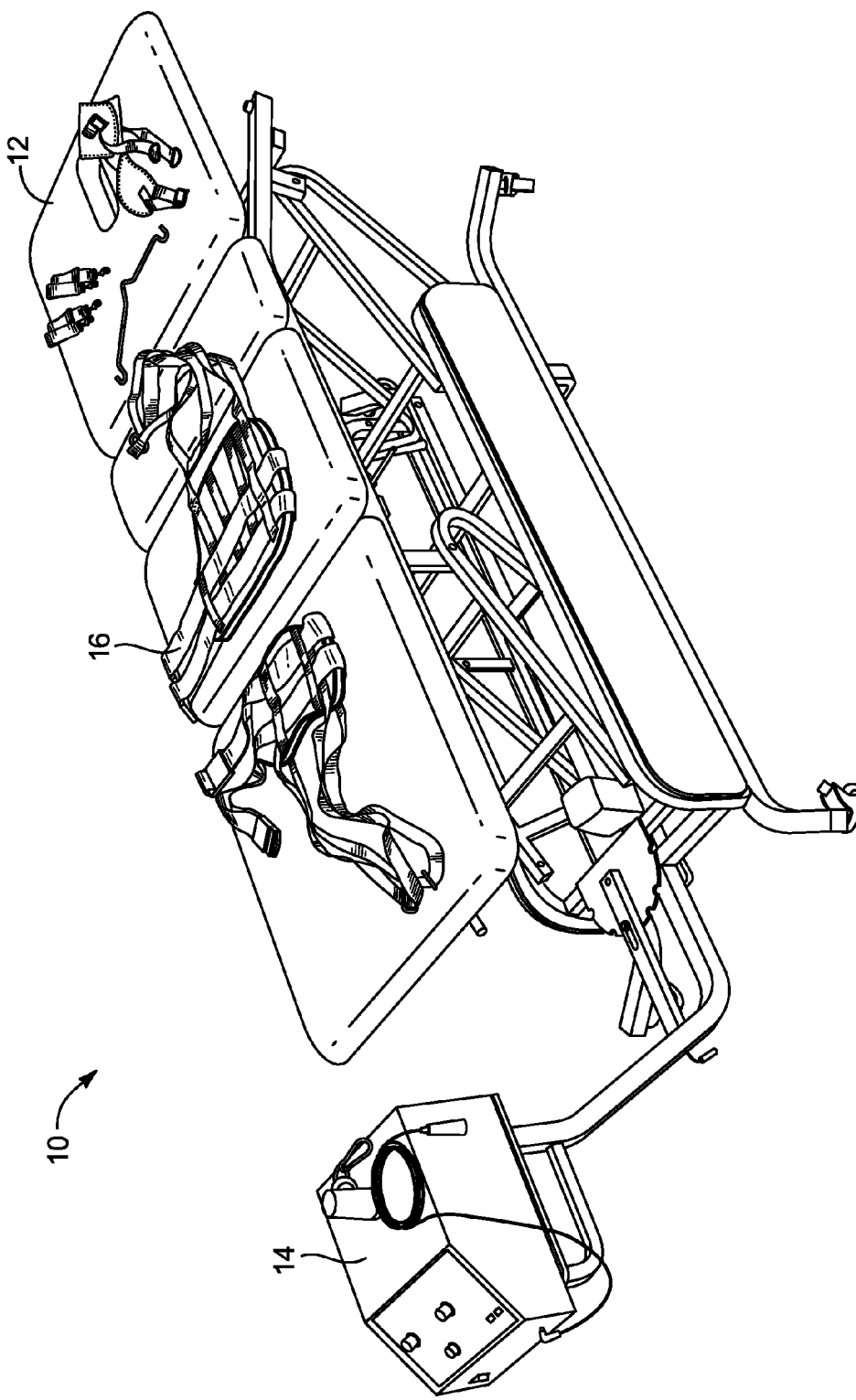
FIG. 1 illustrates a representative traction table for use in association with an embodiment of the present invention.

With reference now to FIG. 1, a representative traction table is illustrated for use in association with an embodiment of the present invention. Traction table 10 comprises surface 12, control system 14 and harness system 16.

Figure 2:
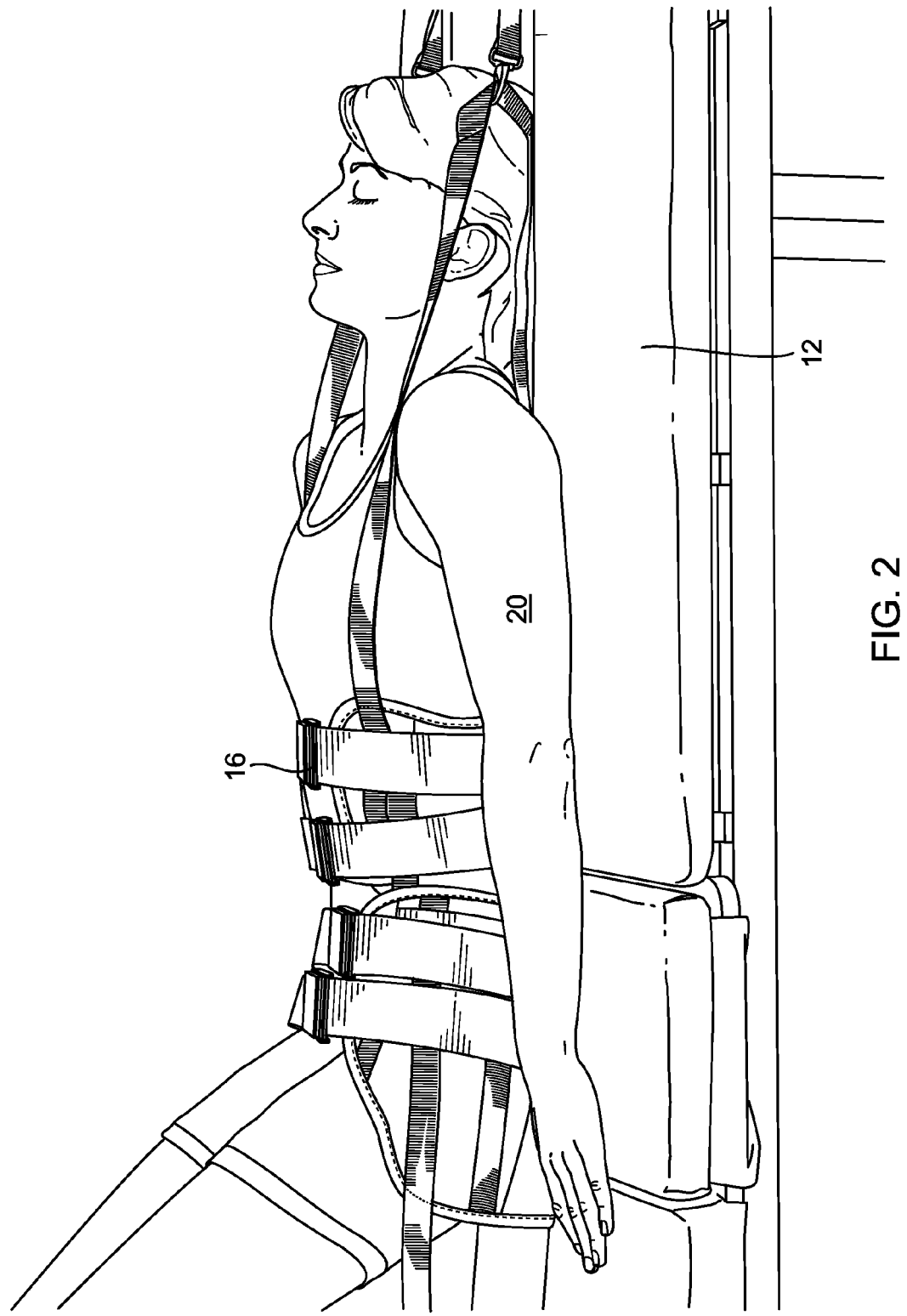
FIG. 2 illustrates a patient receiving traction in association with an embodiment of the present invention.

In FIG. 2, a patient 20 is supported by table 10 and coupled to harness system 16 to selectively administer, for example, lumbar traction to the patient 20. Mechanical traction or decompression can be performed on a patient to provide: (i) vertebral separation, which can decrease intra-discal pressure and reduce bulging of nuclear material and enhance osmosis from vertebral end plates, increasing fluid and blood supply to the discs; (ii) separation and gliding of the facet joints, establishing a potential for improved alignment, articulation, and/or joint mobility; (iii) tensing and/or flexing of the spinal ligaments; (iv) widening of vertebral foramina, allowing increased space for spinal nerve routes; and/or (v) stretching of the spinal muscularature, potentially decreasing its sensitivity to stretch, decreasing muscle spasming and guarding, and/or improving blood supply to posterior soft tissue.

Figure 3:
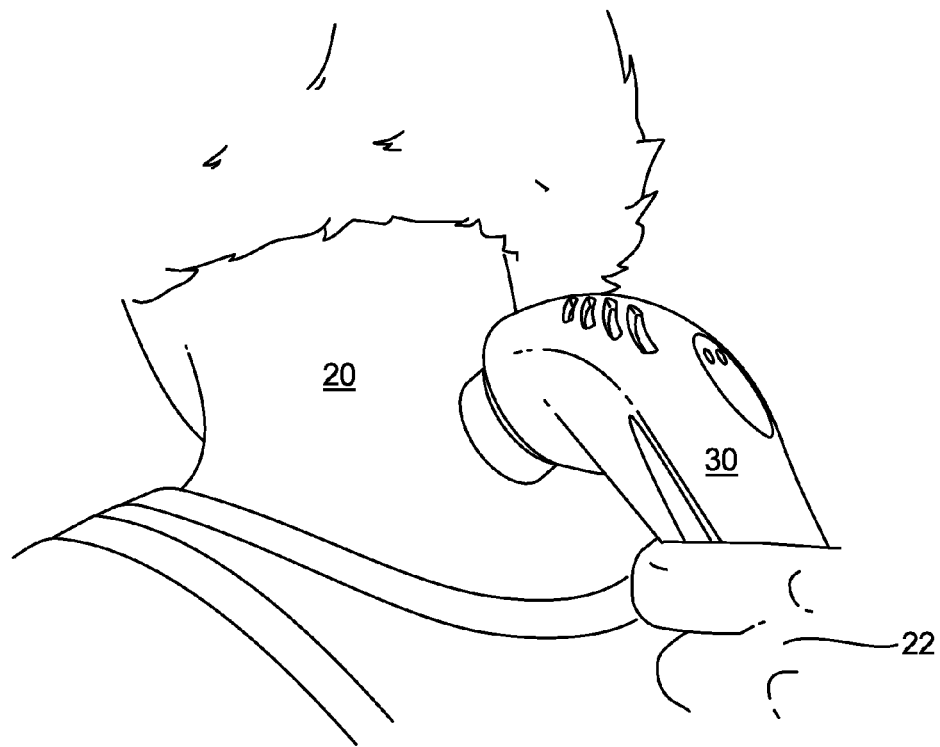
FIG. 3 illustrates a patient receiving light therapy in association with an embodiment of the present invention.

In accordance with embodiments of the present invention, a patient receives traction in combination with light therapy. Accordingly, reference is made to FIG. 3. In FIG. 3, a patient is receiving light therapy in association with an embodiment of the present invention. While the embodiment illustrated in FIG. 3 provides patient 20 receiving light therapy from a caregiver 22 through the use of a light therapy device 30, other embodiments embrace other light therapy devices, including a pad, a scanner, or other attended or unattended light source device that includes one or more light sources configured to deliver light to a patient. In some embodiments, a light source is located in the treatment table. In other embodiments, a light source is located in the harness system.

Figure 4:
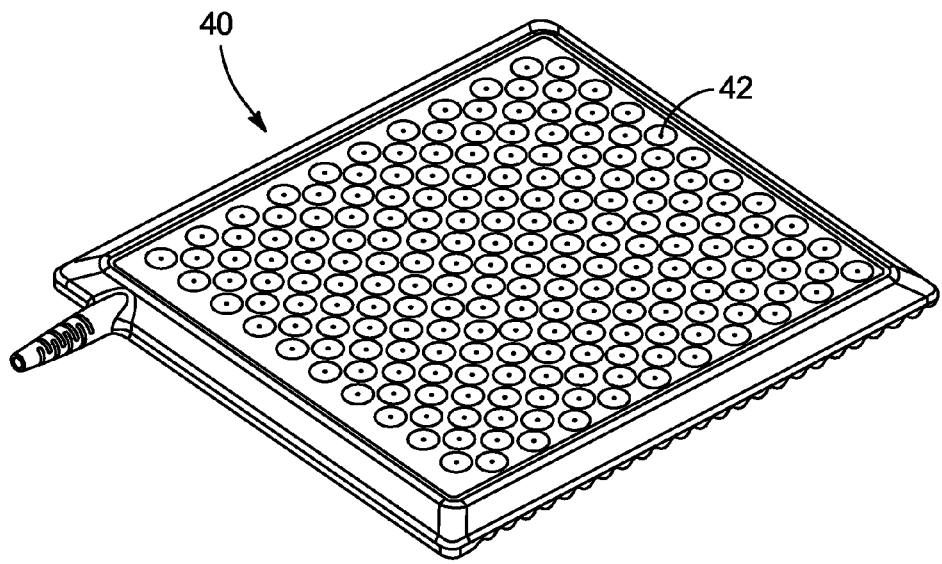
FIG. 4 illustrates another light therapy device for delivering light therapy to a patient in accordance with an embodiment of the present invention.

In FIG. 4, a light pad 40 is illustrated as a light therapy device. Light pad 40 comprises a plurality of light sources, such as LED's, that are configured to provide light therapy to a patient. In one embodiment, light pad 40 is a light therapy pad comprising a flexible, electrical circuit board configuration, a plurality of light sources coupled to the flexible, electrical circuit board configuration, wherein the plurality of light sources are configured to provide light therapy to a patient, and an electrical circuit comprising the plurality of light sources and electrical interconnections of the flexible, electrical circuit board configuration.

The light therapy pad includes a housing configured to receive the flexible, electrical circuit board configuration. In some embodiments, the housing includes a polymer insulating material and a conductive layer. The conductive layer acts as a heat sink, spreading out any heat obtained from electrical components of the flexible, electrical circuit board configuration.

In some embodiments, the flexible, electrical circuit board configuration includes a single flexible PC board. In other implementations, the flexible, electrical circuit board includes a plurality of boards. In some implementations, the flexible, electrical circuit board configuration comprises a plurality of circuit boards that are interconnected by one or more stranded or braided cords. The circuit boards provide increased flexibility of the light pad as bending is allowed between the boards. The cords provide resilient, long-lasting, electrical connections between the independent boards.

In accordance with embodiments of the present invention, light therapy can take place before, during and/or after traction. The light therapy provides, for example, the relaxation of muscles, the relaxation of muscle spasms, and/or the temporary relief of pain, stiffness, and/or minor muscle and joint aches. Additionally, embodiments of the present invention embrace treatment cycles of traction in combination with light therapy.

In one embodiment, a treatment for lumbar decompression comprises treating the lumbar spine with light therapy for approximately under 1 minute to approximately 20 minutes. The patient is then positioned for decompression, with the table being adjusted to achieve the appropriate angle of pull. In one embodiment, a digital or non-digital device, such as an inclinometer, a goniometer, or the like, is used to establish the proper angle. Those skilled in the art will appreciate that other embodiments embrace light therapy for more than 20 minutes.

In some embodiments, lumbar decompression is performed. The following provides representative patient preparation and positioning.

1. Treat lumbar spine with light therapy for approximately 1-20 minutes. (In a further embodiment, the light therapy treatment is performed for 4-9 minutes.)
2. Position the patient for decompression.
3. With the patient on the table, adjust the table height to achieve appropriate angle pull, using the inclinometer to verify the angle. In some embodiments, the traction or decompression is performed for approximately 1-20 minutes.
4. A post treatment of light therapy may be performed for approximately 1-20 minutes.

Those skilled in the art will appreciate that the above sequences and time periods are representative only. Thus, embodiments of the present invention embrace other sequences (e.g., light therapy before, during and/or after traction), and/or time periods that are shorter or longer than the representative embodiment provided above.

The following provides representative treatment angles for anterior conditions, such as a herniated disc, of Lumbar decompression according to some embodiments:

| Anterior Conditions | Treatment Angle |
| --- | --- |
| L5-51 | 10°-15° |
| L4-L5 | 15°-20° |
| L3-L4 | 20°-25° |
| L2-L3 | 30° |

Those skilled in the art will appreciate that the above conditions and angles are representative only. Thus, embodiments of the present invention embrace other treatment angles, including angle ranges having angles that are more acute and/or obtuse than the representative embodiment provided above.

In some embodiments, a treatment angle of 30° is used for lumbar decompression of posterior conditions, such as degenerative disc disease (DDD), muscle spasms, and posterior facet syndrome.

Those skilled in the art will appreciate that the above conditions and angles are representative only. Thus, embodiments of the present invention embrace other treatment angles, including angle ranges having angles that are more acute and/or obtuse than the representative embodiment provided above.

In some embodiments, as the unit approaches the treatment angle and/or the pull strength, the unit slows down to ensure accuracy and/or to provide enhanced treatment results. Additionally, a remote stop cable is provided and given to the patient or caregiver.

In one embodiment, the follow provides a representative set up and treatment for lumbar decompression of anterior conditions:
1. Set Hold/Rest Times—e.g., Hold Time (20 sec.), Rest Time (10 sec.)
2. Set Treatment Time—15 minutes
3. Set Hold Force to 25% of body weight—Over the next 1-2 minutes, increase the traction force in 71b increments until peripheral symptoms decrease up to a maximum of 50% of the body weight. [Note: Start key is to be pressed after each change in Hold Force. Changes will occur at the beginning of the next full Hold cycle.] Once desired Hold Force is achieved, adjust Hold Time to 60 sec. and Rest Force to 80% of Hold Force.
4. Press START.

Those skilled in the art will appreciate that the above sequences, forces and time periods are representative only. Thus, embodiments of the present invention embrace other sequences (e.g., light therapy before, during and/or after traction), force and/or time periods, including forces that are weaker or stronger than the representative embodiment and/or time periods that are shorter or longer than the representative embodiment.

In one embodiment, the follow provides a representative set up and treatment for lumbar decompression of posterior conditions:
1. Set Hold Times—e.g., Hold Time (20 sec.), Rest Time (15 sec.)
2. Set Treatment Time—15 minutes
3. Set Hold Force to 20% of body weight—Over the next 1-2 min., increase the traction force in 71b increments until reaching a comfortable stretch up to a maximum of 33% of the body weight. [Note: Start key is to be pressed after each change in Hold Force. Changes will occur at the beginning of the next full Hold cycle.] Once desired Hold Force is achieved, adjust Hold Time to 45 sec. and Rest Force to 50% of Hold Force.
4. Press START Those skilled in the art will appreciate that the above sequences, forces and time periods are representative only. Thus, embodiments of the present invention embrace other sequences (e.g., light therapy before, during and/or after traction), force and/or time periods, including forces that are weaker or stronger than the representative embodiment and/or time periods that are shorter or longer than the representative embodiment.

In one embodiment, a treatment for cervical decompression comprises treating the lumbar spine with light therapy for approximately 1-20 minutes. The table height is adjusted to achieve appropriate angle of pull. An inclinometer may be used to verify the proper angle. For example, in one embodiment, a treatment angle of 25° is used for anterior conditions, such as a herniated disc. In one embodiment, a treatment angle of 30° is used for posterior conditions, such as degenerative disc disease (DDD), muscle spasms, or posterior facet syndrome. The patient is positioned in the cervical device, and a remote stop cable is provided to the patient. Those skilled in the art will appreciate that the above embodiments are representative only. Thus, other embodiments embrace light therapy for more than 20 minutes and/or angles that are more acute or obtuse than the treatment angles provided above.

In one embodiment, the follow provides a representative set up and treatment for cervical decompression of anterior conditions:
1. Set Hold Times—e.g., Hold Time (20 sec.), Rest Time (10 sec.)
2. Set Treatment Time—12 minutes
3. Set Hold Force to (20-40 lb. range)—Set Hold Force to 15 lbs. Set Rest Force to 12 lbs. (80% of Hold Force). Over the next 1-2 min., increase the traction force in 3 lb. increments until maximum comfortable pull force is achieved (usually 20-40 lbs.). Typically, observed peripheral symptoms will decrease. [Note: Start key must be pressed after each change in Hold Force. Changes will occur at the beginning of the next full Hold cycle.] Once desired Hold Force is achieved, adjust Hold Time to 60 sec. and Rest Force to 80% of Hold Force.
4. Press START Those skilled in the art will appreciate that the above sequences, forces and time periods are representative only. Thus, embodiments of the present invention embrace other sequences (e.g., light therapy before, during and/or after traction), force and/or time periods, including forces that are weaker or stronger than the representative embodiment and/or time periods that are shorter or longer than the representative embodiment.

In one embodiment, the follow provides a representative set up and treatment for cervical decompression of posterior conditions:
1. Set Hold Times—e.g., Hold Time (20 sec.), Rest Time (15 sec.)
2. Set Treatment Time—15 minutes
3. Set Hold Force to a comfortable stretch (10-20 lb. range)—Over the next 1-2 min., increase the traction force in 3 lb. increments up to a comfortable stretch (maximum of 20 lbs.). [Note: Start key must be pressed after each change in Hold Force. Changes will occur at the beginning of the next full Hold cycle.] Once desired Hold Force is achieved, adjust Hold Time to 45 sec. and Rest Force to 50% of Hold Force.
4. Press START Those skilled in the art will appreciate that the above sequences, forces and time periods are representative only. Thus, embodiments of the present invention embrace other sequences (e.g., light therapy before, during and/or after traction), force and/or time periods, including forces that are weaker or stronger than the representative embodiment and/or time periods that are shorter or longer than the representative embodiment.

Figure 5:
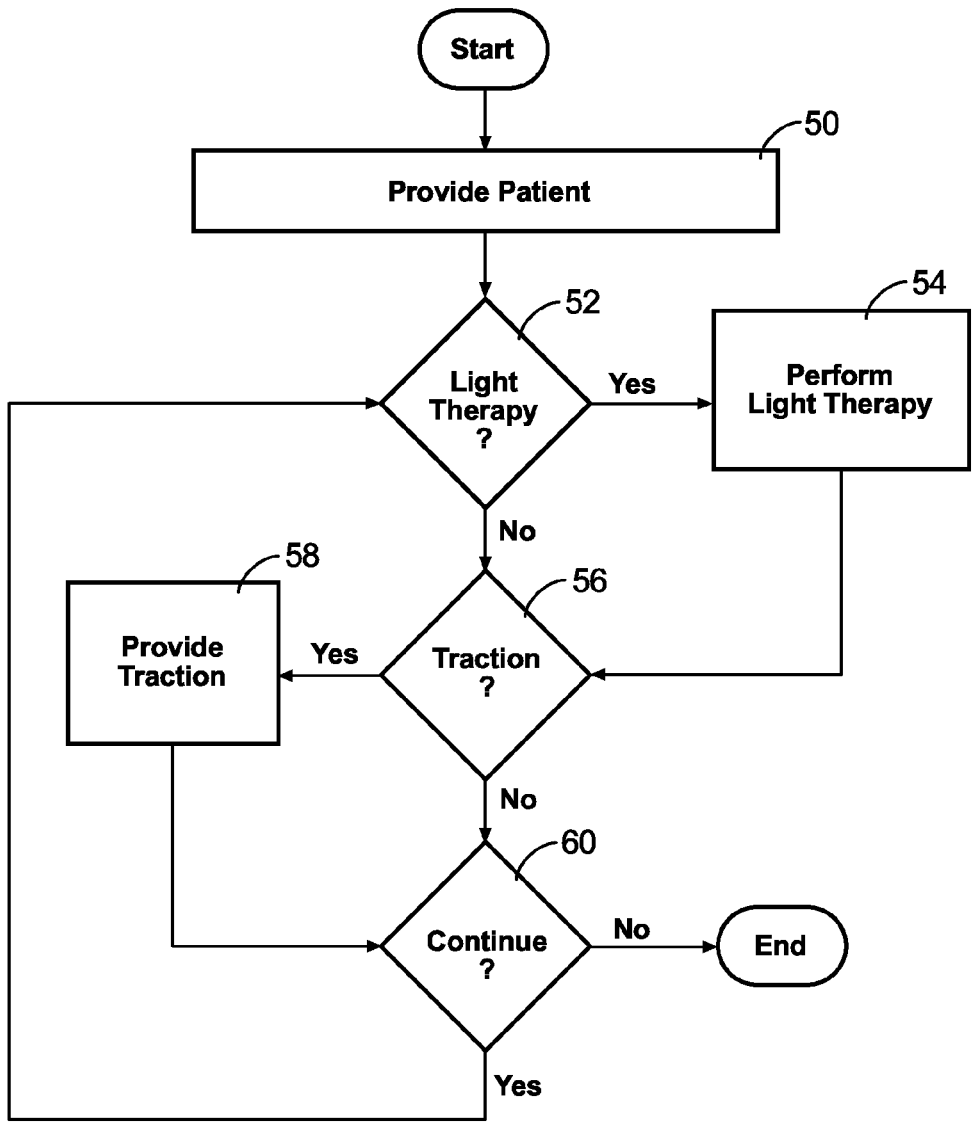
FIG. 5 illustrates a representative method for providing light therapy traction in association with an embodiment of the present invention.

FIG. 5 illustrates a representative method for providing light therapy traction in association with the present invention. In FIG. 5, execution begins at step 50, wherein a patient is provided for treatment. A determination is made at decision block 52 as to whether or not the patient is to receive light therapy. If it is determined at decision block 52 that the patient is to receive light therapy at this time, execution begins to step 54 for the performance of the light therapy. Alternatively, if it is determined at decision block 52 that the patient is not to receive light therapy at this time, execution proceeds directly to decision block 56. At decision block 56 a determination is made as to whether or not a patient is to receive traction at this time. If it is determined at decision block 56 that the patient is to receive traction, the traction is provided as step 58 and execution then proceeds to decision block 60. Alternatively, if it is determined at decision block 56 that the patient is not to receive traction at this time, execution proceeds directly to decision block 60. At decision block 60 a determination is made as to whether or not the treatment is to continue or otherwise for a subsequent cycle to take place in the treatment. Accordingly, if it is determined at decision block 60 that the treatment is to continue or that a subsequent cycle is to take place, execution returns back to decision block 52.

In traction, a mechanical connection is made between the traction line and the patient, and an angle is inferred. A sensor is used to give an output that tells the angle of the traction line being pulled. The traction relieves pressure and causes separation between the patient's disc space. The angle allows the traction to be focused at a particular area.

Adjustment of the angle of the traction line isolates a particular spinal segment. Thus, the angle of the pull affects the treatment. One embodiment of the present invention includes a sensor in the top of a traction head so as the traction line changes the pull angle, the sensor measures the angle and displays it digitally on an output screen. In one embodiment, the adjustment is automated.

As provided herein, light therapy is used in conjunction with traction to reduce muscle spasm. This reduces the number of muscles that are trying to be stretched but are locked up because they are in spasm. Light therapy when applied to a lower back in spasm will relax those muscles and break the spasm. So, pretreatment with light therapy before traction provides a better result.

In accordance with some embodiments of the present invention, a light therapy lumbar system includes a computer device. For example, utilization of a computer device can provide accuracy in treatment, such as angle, force, and/or timing accuracy. Accordingly, FIG. 6 and the corresponding discussion thereto pertain to a representative computer device for use in accordance with an embodiment of the present invention. One skilled in the art will appreciate that the invention may be practiced by one or more computing devices and in a variety of system configurations, including in a networked configuration.

Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

Figure 6:
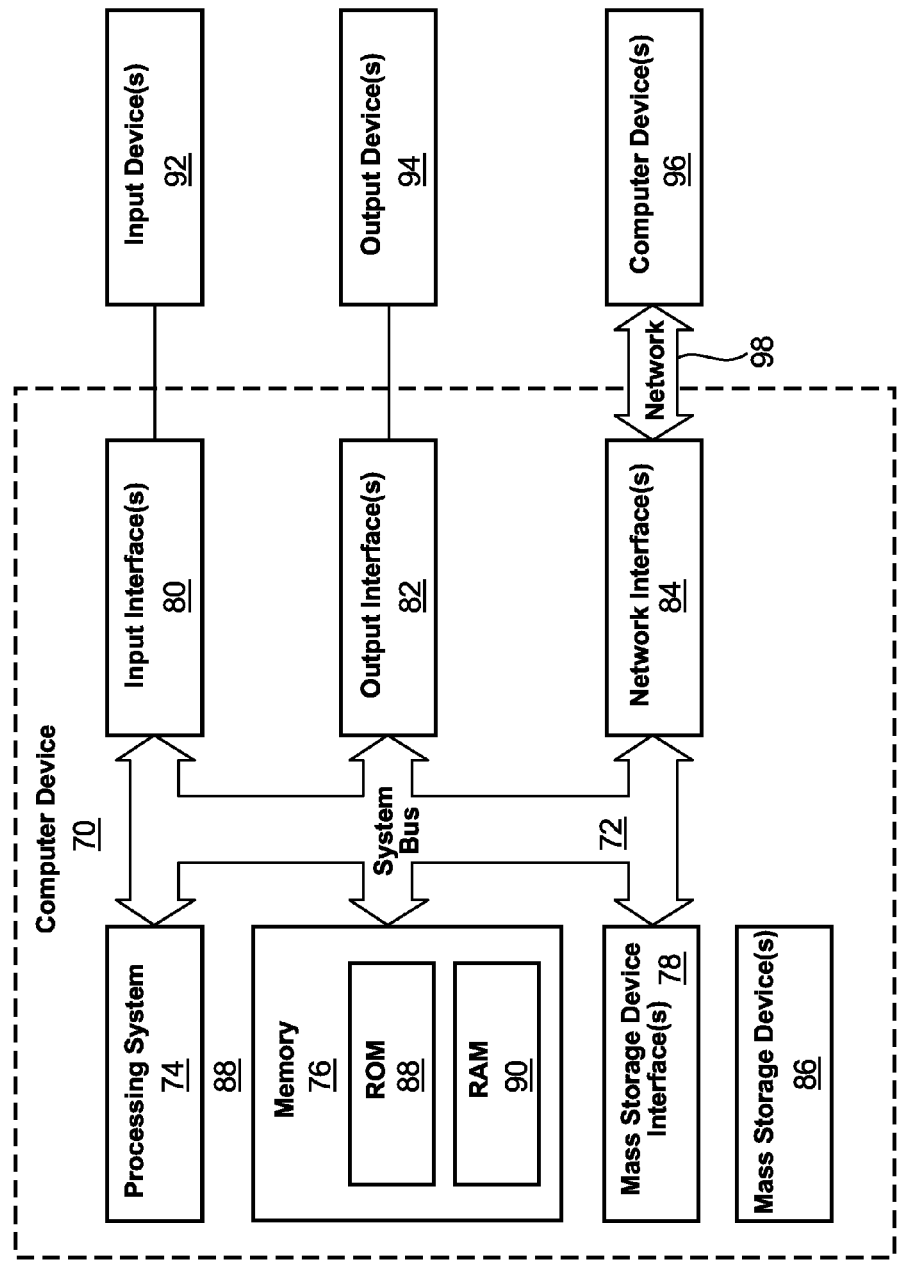
FIG. 6 illustrates a representative computer device for use in accordance with an embodiment of the present invention.

With reference to FIG. 6, a representative system for implementing the invention includes computer device 70, which may be a general-purpose or special-purpose computer. For example, computer device 70 may be a personal computer, a notebook computer, a personal digital assistant ("PDA") or other hand-held device, a workstation, a minicomputer, a mainframe, a supercomputer, a multi-processor system, a network computer, a processor-based consumer electronic device, or the like.

Computer device 70 includes system bus 72, which may be configured to connect various components thereof and enables data to be exchanged between two or more components. System bus 72 may include one of a variety of bus structures including a memory bus or memory controller, a peripheral bus, or a local bus that uses any of a variety of bus architectures. Typical components connected by system bus 72 include processing system 74 and memory 76. Other components may include one or more mass storage device interfaces 78, input interfaces 80, output interfaces 82, and/or network interfaces 84, each of which will be discussed below.

Processing system 74 includes one or more processors, such as a central processor and optionally one or more other processors designed to perform a particular function or task. It is typically processing system 74 that executes the instructions provided on computer readable media, such as on memory 76, a magnetic hard disk, a removable magnetic disk, a magnetic cassette, an optical disk, or from a communication connection, which may also be viewed as a computer readable medium.

Memory 76 includes one or more computer readable media that may be configured to include or includes thereon data or instructions for manipulating data, and may be accessed by processing system 74 through system bus 72. Memory 76 may include, for example, ROM 88, used to permanently store information, and/or RAM 90, used to temporarily store information. ROM 88 may include a basic input/output system ("BIOS") having one or more routines that are used to establish communication, such as during start-up of computer device 70. RAM 90 may include one or more program modules, such as one or more operating systems, application programs, and/or program data.

One or more mass storage device interfaces 78 may be used to connect one or more mass storage devices 86 to system bus 72. The mass storage devices 86 may be incorporated into or may be peripheral to computer device 70 and allow computer device 70 to retain large amounts of data. Optionally, one or more of the mass storage devices 86 may be removable from computer device 70. Examples of mass storage devices include hard disk drives, magnetic disk drives, tape drives, solid state mass storage, and optical disk drives. Examples of mass storage devices include hard disk drives, magnetic disk drives, tape drives and optical disk drives. Examples of solid state mass storage include flash cards and memory sticks. A mass storage device 86 may read from and/or write to a magnetic hard disk, a removable magnetic disk, a magnetic cassette, an optical disk, or another computer readable medium. Mass storage devices 86 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 80 may be employed to enable a user to enter data and/or instructions to computer device 70 through one or more corresponding input devices 92. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 80 that may be used to connect the input devices 92 to the system bus 72 include a serial port, a parallel port, a game port, a universal serial bus ("USB"), a firewire (IEEE 1394), or another interface.

One or more output interfaces 82 may be employed to connect one or more corresponding output devices 94 to system bus 72. Examples of output devices include a monitor or display screen, a speaker, a printer, and the like. A particular output device 94 may be integrated with or peripheral to computer device 70. Examples of output interfaces include a video adapter, an audio adapter, a parallel port, and the like.

One or more network interfaces 84 enable computer device 70 to exchange information with one or more other local or remote computer devices, illustrated as computer devices 96, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 84 may be incorporated with or peripheral to computer device 70. In a networked system, accessible program modules or portions thereof may be stored in a remote memory storage device. Furthermore, in a networked system computer device 70 may participate in a distributed computing environment, where functions or tasks are performed by a plurality of networked computer devices. While those skilled in the art will appreciate that the invention may be practiced in networked computing environments with many types of computer system configurations.

Thus, as discussed herein, the embodiments of the present invention embrace optimizing traction treatments. In particular, the present invention relates to systems and methods for providing light therapy cervical and/or lumbar traction to a patient.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method for treating a treatment area of a patient, the method comprising:
   pretreating a treatment area of a patient's body with a first light therapy treatment, wherein the pretreating occurs before the treatment area is decompressed using a first application of traction;
   decompressing the pretreated treatment area of the patient's body; and
   delivering a second light therapy treatment to the treatment area of the patient's body concomitant to the decompression of the pretreated treatment area, wherein the steps of pretreating the treatment area, decompressing the pretreated treatment area, and concomitant delivery the second light therapy treatment to the decompressed, pretreated treatment area comprise a treatment cycle.

2. A method as recited in claim 1, wherein the step of decompressing the pretreated treatment area of the patient's body comprises a plurality of treatment angles, pull strengths, pull times, and rest times.

3. A method as recited in claim 2, wherein the step of decompressing the pretreated treatment area of the patient's body further comprises:
   selecting a first treatment angle;
   selecting a first pull strength;
   selecting a first pull time;
   selecting a first rest time;
   applying the first pull strength to the pretreated treatment area of the patient's body to effect the first treatment angle for the first pull time; and
   relaxing the pretreated treatment area of the patient's body for the first rest time.

4. A method as recited in claim 3, wherein the first pull strength is applied to the pretreated treatment area in a plurality of increments.

5. A method as recited in claim 1, further comprising:
   relaxing the treatment area following completion of said delivering a second light therapy treatment; and
   delivering a third light therapy treatment to the relaxed treatment area.

6. A method as recited in claim 5, wherein the relaxed treatment area is treated with the third light therapy treatment from about one minute to about 20 minutes.

7. A method as recited in claim 1, wherein the treatment area is pretreated from about a minute to about twenty minutes.

8. A method as recited in claim 1, wherein the treatment area is pretreated from about four minutes to about nine minutes.

9. A method as recited in claim 1, wherein the treatment area is concomitantly decompressed and treated with a second light therapy treatment from about one minute to about twenty minutes.

10. A method as recited in claim 1, wherein the step of decompressing the pretreated area of the patient's body is performed within about sixty minutes following the step of pretreating the treatment area of the patient's body.

11. A method as recited in claim wherein the treatment cycle is repeated on the treatment area.

12. A method as recited in claim 1, wherein the treatment cycle is for at least one of:

| | |
|---|---|
| (i) | chronic pain; |
| (ii) | a tension headache; |
| (iii) | a migraine headache; |
| (iv) | atypical facial pain; |
| (v) | a TMJ disorder; |
| (vi) | fibromyalgia; |
| (vii) | osteoarthritis; |
| (viii) | rheumatoid arthritis; |
| (ix) | pain associated with arthritis; |
| (x) | stiffness associated with arthritis; |
| (xi) | increasing local blood circulation; |
| (xii) | muscle spasm; |
| (xiii) | joint pain; |
| (xiv) | inflammation; |
| (xv) | Raynaud's Syndrome; |
| (xvi) | reflex sympathetic dystrophy; |
| (xvii) | a burn; |
| (xviii) | occipital neuralgia; |
| (xix) | neck-shoulder paid; |
| (xx) | frozen shoulder; |

-continued

| | |
|---|---|
| (xxi) | medial epicondylitis; |
| (xxii) | lateral epicondylitis; |
| (xxiii) | carpal tunnel syndrome; |
| (xxiv) | costochondritis; |
| (xxv) | spondylitis; |
| (xxvi) | low back strain; |
| (xxvii) | sciatica; |
| (xxviii) | hip arthritis; |
| (xxix) | knee arthritis; |
| (xxx) | an injury; |
| (xxxi) | a post surgical procedure; |
| (xxxii) | a post traumatic procedure; |
| (xxxiii) | achilles tendonitis; |
| (xxxiv) | an ankle sprain; |
| (xxxv) | plantar fasciitis; |
| (xxxvi) | shingles; and |
| (xxxvii) | postherpetic neuralgia. |

13. A method for providing traction treatment to a patient, the method comprising:
pretreating a treatment region of a patient's body with a first light therapy treatment;
coupling a traction system to a patient;
applying a second light therapy treatment to the treatment region of the patient's body to relax a muscle group within the treatment region; and
activating the traction system to perform a first application of traction on the treatment region, wherein the pretreating occurs before the first application of traction.

14. A method as recited in claim 13, wherein the step of activating the traction system to perform traction on the treatment region further comprises:
aligning the traction system to establish a particular angle between a traction line of the traction system and the treatment region of the patient's body; and
providing a force along the traction line to perform traction on a particular portion of the treatment region at a desired treatment angle.

15. A method as recited in claim 14, wherein the desired treatment angle for an anterior condition is from about 10° to about 30°.

16. A method as recited in claim 14, wherein the step of activating the traction system to perform traction is performed within about sixty minutes following the step of pretreating the treatment area of the patient's body.

17. A method as recited in claim 14, further comprising simultaneous application of the second light therapy treatment and traction to the treatment region of the patient's body.

18. A method for delivering light therapy traction to a patient, the method comprising:
providing a traction device;
providing a light therapy device;
providing a computer program product for controlling the traction device and the light therapy device to implement delivery of light therapy traction to a patient; and
pretreating a treatment area of a patient's body with a first light therapy treatment wherein the pretreating occurs before the treatment area is decompressed using a first application of traction.

19. A method as recited in claim 18, wherein the computer program product comprises a computer readable medium for providing computer program code means utilized to implement delivery of light therapy traction.

20. A method as recited in claim 19, wherein the computer program code means is comprised of executable code for implementing the steps for:
initiating a second light therapy treatment to the treatment area of the patient's body; and
initiating traction at a particular angle to concentrate a traction force on the treatment area of the patient's body, wherein the steps of delivering the second light therapy treatment and administering traction comprise a treatment cycle.

* * * * *